(12) United States Patent
Lee et al.

(10) Patent No.: US 11,833,260 B2
(45) Date of Patent: Dec. 5, 2023

(54) STERILIZATION SYSTEM FOR VEHICLE

(71) Applicants: Hyundai Motor Company, Seoul (KR); Kia Motors Corporation, Seoul (KR); KAIS Inc., Pyeongtaek-si (KR)

(72) Inventors: Jae Seung Lee, Hwaseong-si (KR); Young Hoon Ji, Osan-si (KR)

(73) Assignees: Hyundai Motor Company, Seoul (KR); Kia Motors Corporation, Seoul (KR); KAIS Inc., Pyeongtaek-si (KR)

( * ) Notice: Subject to any disclaimer, the term of this patent is extended or adjusted under 35 U.S.C. 154(b) by 270 days.

(21) Appl. No.: 17/154,600

(22) Filed: Jan. 21, 2021

(65) Prior Publication Data

US 2022/0080063 A1 Mar. 17, 2022

(30) Foreign Application Priority Data

Sep. 15, 2020 (KR) .................. 10-2020-0118490

(51) Int. Cl.
*A61L 2/10* (2006.01)
*B60S 1/64* (2006.01)
*A61L 2/26* (2006.01)

(52) U.S. Cl.
CPC ............ *A61L 2/10* (2013.01); *A61L 2/26* (2013.01); *B60S 1/64* (2013.01); *A61L 2202/11* (2013.01); *A61L 2202/25* (2013.01)

(58) Field of Classification Search
CPC .......... A61L 2/10; A61L 2/26; A61L 2202/11; A61L 2202/25; B60S 1/64
See application file for complete search history.

(56) References Cited

U.S. PATENT DOCUMENTS

| 2005/0047142 A1* | 3/2005 | Lui | B60Q 1/245 362/286 |
| 2015/0276190 A1* | 10/2015 | Devlin | F21V 21/30 362/362 |
| 2020/0061223 A1* | 2/2020 | Hallack | B60N 2/002 |

FOREIGN PATENT DOCUMENTS

| CN | 208365304 U | * | 1/2019 | ............. F21S 8/026 |
| KR | 20110116667 A | * | 10/2011 | |
| KR | 20200008100 A | | 1/2020 | |
| WO | WO-2019175751 A1 | * | 9/2019 | ............. F21S 8/026 |

* cited by examiner

Primary Examiner — Kevin Joyner
Assistant Examiner — Justin Hwang
(74) Attorney, Agent, or Firm — Slater Matsil, LLP

(57) ABSTRACT

A sterilization system for a vehicle includes an outer housing configured to rotate about a first shaft and having an opening formed to face an interior space, an inner housing installed inside the outer housing, exposed to the interior space through the opening, configured to rotate about a second shaft, and having a light transmitting portion through which sterilizing light is transmitted, a light source embedded in the inner housing and configured to irradiate the sterilizing light toward the light transmitting portion, and a driver configured to rotate the outer housing and the inner housing to irradiate the sterilizing light to the interior space and to change an irradiation angle of the sterilizing light.

20 Claims, 12 Drawing Sheets

STERILIZATION SYSTEM FOR VEHICLE

CROSS-REFERENCE TO RELATED APPLICATIONS

This application claims priority to Korean Patent Application No. 10-2020-0118490, filed on Sep. 15, 2020, which application is hereby incorporated herein by reference.

TECHNICAL FIELD

The present disclosure relates to a sterilization system for a vehicle.

BACKGROUND

In response to exposure to infectious diseases such as influenza and corona in a vehicle, many technologies have recently been discussed to prevent such diseases. It is now known that the most effective way to eradicate bacteria in the vehicle is to irradiate ultraviolet (UV) rays directly to the bacteria.

However, the ultraviolet rays may cause adverse effects such as skin cancers when irradiated directly to a human body. Thus, it is necessary to effectively remove only the bacteria by irradiating the ultraviolet rays to the inside of the vehicle, while avoiding irradiating the ultraviolet rays to the human body, only in special cases.

Meanwhile, concerning an interior trim of the vehicle, it is generally advantageous not only in design but also in collision-related safety that the interior trim has a flat surface without a protrusion.

Accordingly, there is a need for a mechanical system capable of irradiating ultraviolet rays to the interior trim of the vehicle while avoiding irradiating the ultraviolet rays directly to the human body, and forming a plane on the same level as the interior trim of the vehicle when the system is not used taking design into consideration.

The contents described in the background section have been provided only to assist in understanding the background of the present disclosure and should not be considered as corresponding to the related art known to those having ordinary skill in the art.

SUMMARY

The present disclosure relates to a sterilization system for a vehicle. Particular embodiments relate to a sterilization system for a vehicle capable of removing contamination caused by bacteria or the like in the inside of the vehicle, sterilizing several points at the same time, and preventing the user from feeling uncomfortable while being excellent in terms of design by forming a plane on the same level as an interior trim of the vehicle when the sterilization system is not used.

An embodiment of the present disclosure provides a sterilization system for a vehicle capable of removing contamination caused by bacteria or the like in the inside of the vehicle, sterilizing several points at the same time, and preventing the user from feeling uncomfortable while being excellent in terms of design by forming a plane on the same level as an interior trim of the vehicle when the sterilization system is not used.

According to an embodiment of the present disclosure, a sterilization system for a vehicle includes an outer housing rotated about a first shaft and having an opening formed to face an interior space, an inner housing installed inside the outer housing, exposed to the inside of the vehicle through the opening, rotated about a second shaft, and having a light transmitting portion through which sterilizing light is transmitted, a light source embedded in the inner housing and irradiating the sterilizing light toward the light transmitting portion, and a driving unit or driver rotating the outer housing and the inner housing to irradiate the sterilizing light to the interior space of the vehicle and to change an irradiation angle of the irradiated sterilizing light.

The outer housing may have a hemispherical shape with the opening and be inserted into an interior trim of the vehicle, and the opening may be disposed to face the interior space of the vehicle.

The first shaft of the outer housing may be set to be directed toward an irradiation target to which the sterilizing light is irradiated, and the outer housing may be rotated about the first shaft when the driving unit drives the outer housing.

The inner housing may have a spherical shape to be rotated inside the outer housing, and the second shaft may be disposed to cross and intersect with the first shaft.

The outer housing may have a guide slit extending along a rotational trajectory of the inner housing, the inner housing may have a guide protrusion protruding outwardly, and the guide protrusion may slide while being guided by the guide slit when the inner housing is rotated.

The sterilization system may further include a system housing surrounding the outer housing. The system housing may have an outer slit formed to overlap the guide slit, the outer slit may be formed with an extension bent and extending in a lateral direction from an end of the outer slit, and the guide protrusion may slide while being guided by the outer slit when the inner housing is rotated and laterally slide while being guided by the extension when the outer housing is rotated.

The inner housing may be rotated about the second shaft to expose or not to expose the light transmitting portion to the interior space of the vehicle.

The outer housing may be rotated about the first shaft to change an irradiation target toward which the light transmitting portion is directed in the interior space of the vehicle.

The driving unit may be connected to the first shaft of the outer housing through a first driving gear and connected to the second shaft of the inner housing through a second driving gear.

The driving unit may rotate in one direction to rotate the inner housing first through the second driving gear, and continue to rotate in the one direction to rotate the outer housing thereafter through the first driving gear.

The driving unit may include a motor and a rotator rotated by the motor, and the first driving gear and the second driving gear may be formed on an outer circumferential surface of the rotator at positions spaced apart from each other in a circumferential direction, respectively.

A first pinion gear may be provided on the first shaft of the outer housing and a second pinion gear may be provided on the second shaft of the inner housing, and when the rotator rotates, the first driving gear may be connected to the first pinion gear or the second driving gear is connected to the second pinion gear.

DETAILED DESCRIPTION OF ILLUSTRATIVE EMBODIMENTS

Figure 1:
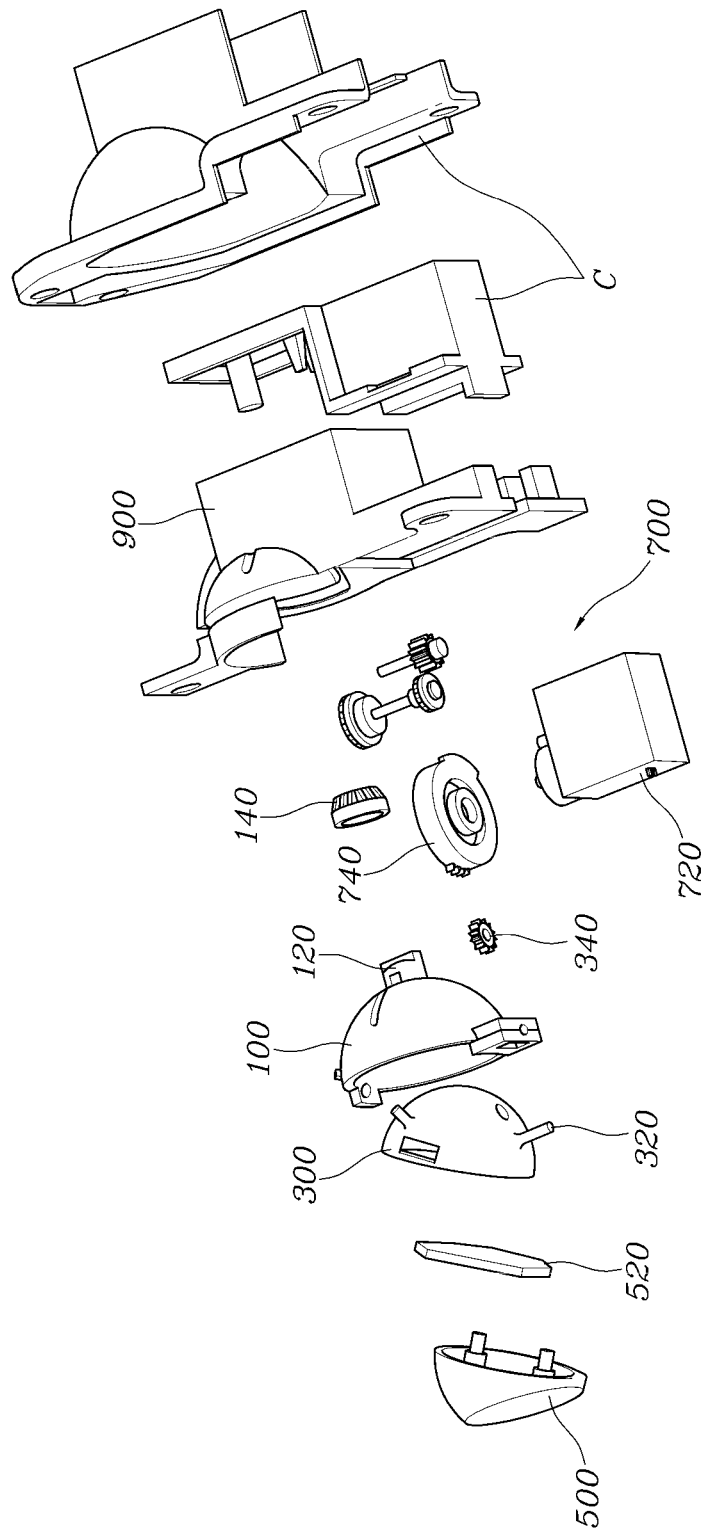
FIG. 1 is an exploded perspective view of a sterilization system for a vehicle according to an embodiment of the present disclosure.
Figure 2:
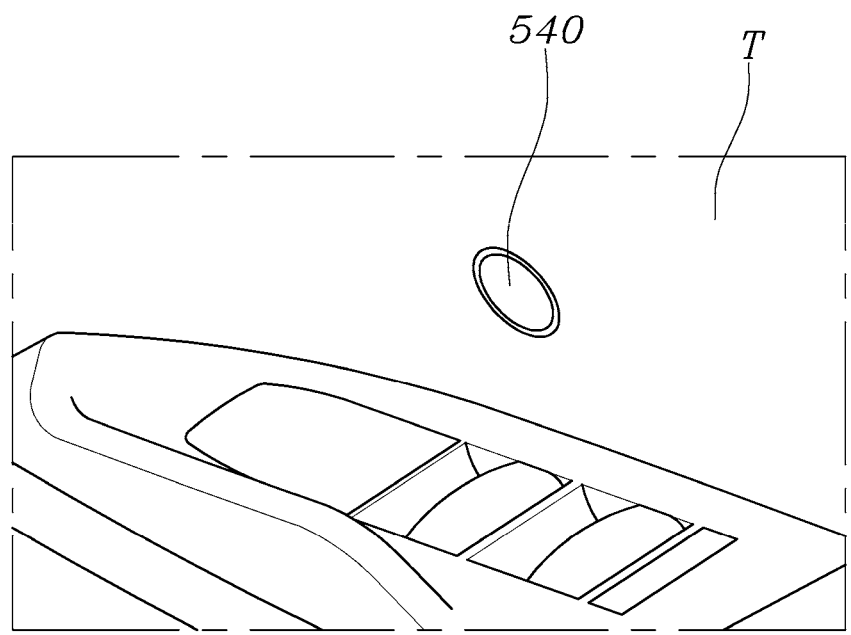
FIGS. 2 to 4 are views illustrating operation processes of the sterilization system for a vehicle according to an embodiment of the present disclosure.
Figure 3:
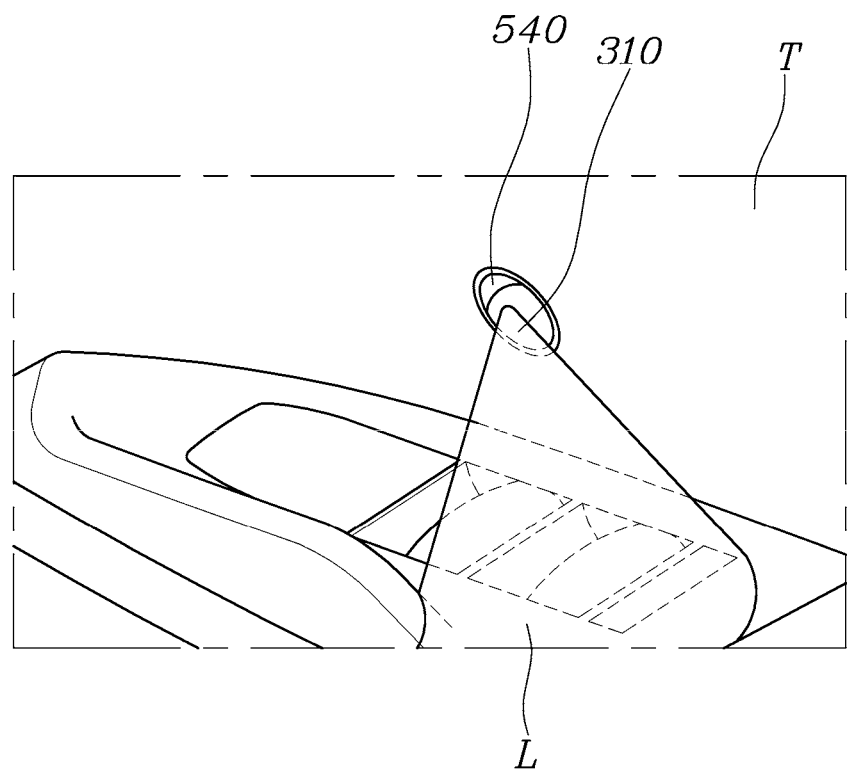
Figure 4:
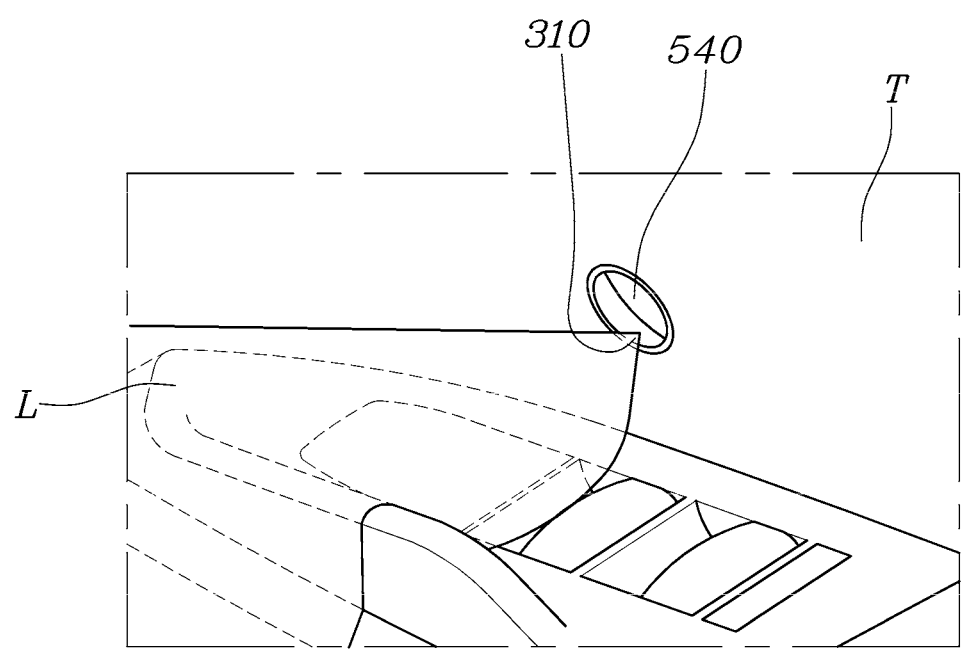
Figure 5:
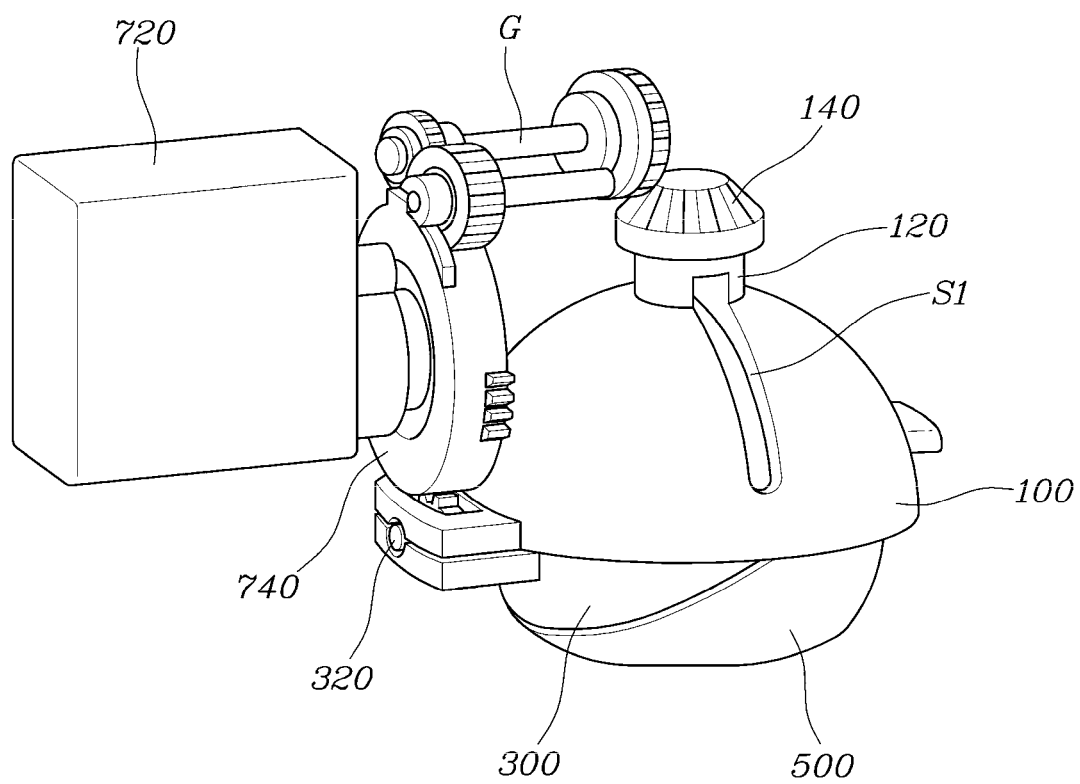
FIGS. 5 to 12 are views sequentially illustrating operation principles of the sterilization system for a vehicle according to an embodiment of the present disclosure.

FIG. 1 is an exploded perspective view of a sterilization system for a vehicle according to an embodiment of the present disclosure. FIGS. 2 to 4 are views illustrating operation processes of the sterilization system for a vehicle according to an embodiment of the present disclosure. FIGS. 5 to 12 are views sequentially illustrating operation principles of the sterilization system for a vehicle according to an embodiment of the present disclosure.

FIGS. 2 to 4 are views illustrating operation processes of the sterilization system for a vehicle according to an embodiment of the present disclosure. As illustrated in FIG. 2, the sterilization system for a vehicle according to the present disclosure is normally stored in an interior trim T of the vehicle on the same plane as the interior trim T. When the interior trim needs to be sterilized, the sterilization system rotates to irradiate sterilizing light L, such as ultraviolet rays, to the trim (including switches touched by a hand) as shown in FIG. 3, and continues to rotate to sterilize several areas as shown in FIG. 4. In addition, when sterilization is not required or a user's body is close to the sterilization system, the sterilization system returns back to the stored state as shown in FIG. 1.

That is, when the user is not in the vehicle or when the user is far away from the sterilization system even though the user is in the vehicle, the sterilization system is exposed to the outside to irradiate sterilizing light such as ultraviolet rays, thereby directly eradicating bacteria existing on a surface of the trim. In addition, the sterilizing light may be irradiated to several points by rotating the sterilization system, thereby effectively sterilizing the surroundings. In particular, when the sterilization system is not used, it is stored on the same plane as the interior trim without being exposed, resulting in great effects in terms of design, safety, and convenience.

The sterilization system for a vehicle according to embodiments of the present disclosure as described above may be provided in a door, a roof, a side and the like of the vehicle to selectively sterilize several points touched by the user's body, such as steering devices, various kinds of switches, a handle and seats.

Specifically, FIG. 1 is an exploded perspective view of the sterilization system for a vehicle according to an embodiment of the present disclosure, and FIGS. 5 to 12 are views sequentially illustrating operation principles of the sterilization system for a vehicle according to an embodiment of the present disclosure.

The sterilization system for a vehicle according to embodiments of the present disclosure includes an outer housing 100 installed in the interior trim T of the vehicle, rotated about a first shaft 120, and having an opening formed to face an interior space. An inner housing 300 is installed inside the outer housing 100, is exposed to the inside of the vehicle through the opening, is rotated about a second shaft 320, and has a light transmitting portion 310 through which sterilizing light L is transmitted. A light source 520 is embedded in the inner housing 300 and irradiates the sterilizing light L toward the light transmitting portion 310, and a driving unit 700 rotates the outer housing 100 and the inner housing 300 to irradiate the sterilizing light L to the interior space of the vehicle and to change an irradiation angle of the irradiated sterilizing light L. A cover 500 may be disposed in a direction opposite to the inner housing 100 based on the light source 520.

The sterilization system for a vehicle according to embodiments of the present disclosure is installed in the interior trim T of the vehicle, as illustrated in FIG. 2. A bracket C is provided on the outermost side of the sterilization system for a vehicle, and a system housing 900 is installed on the bracket C. The system housing 900 is fixed to a vehicle body or the like through the bracket C. The outer housing 100 is provided in the system housing 900. The outer housing 100 is rotated about the first shaft 120 and has an opening formed to face the interior space. Specifically, the outer housing 100 may have a hemispherical shape with the opening and be inserted into the interior trim T of the vehicle and installed in the system housing 900, and the opening may be disposed to face the interior space of the vehicle.

The inner housing 300 is installed inside the outer housing 100. The inner housing 300 is exposed to the inside of the vehicle through the opening of the outer housing 100. The inner housing 300 is rotated about the second shaft 320, and the light transmitting portion 310 through which sterilizing light L is transmitted is formed therein. Thus, the inner housing 300 may be rotated to expose or not to expose the light transmitting portion 310 to the inside of the vehicle, thereby fundamentally avoiding the problem of irradiating the sterilizing light to a human body and storing the sterilization system on the same plane as the trim when the sterilization system is not used.

The light source 520 is embedded in the inner housing 300. The light source 520 irradiates sterilizing light toward the light transmitting portion 310. The light source 520 includes a printed circuit board (PCB) and an ultraviolet light emitting diode (LED) lamp.

The driving unit 700 rotates the outer housing 100 and the inner housing 300 to irradiate the sterilizing light to the interior space of the vehicle and to change an irradiation angle of the irradiated sterilizing light. That is, the sterilization system is exposed to the inside of the vehicle by operating the driving unit 700 as illustrated in FIG. 3 from the state of FIG. 2 where only a face 520 of the cover 500 is exposed, and also a region to which the sterilizing light L is irradiated is changed from the state of FIG. 3 to a state of FIG. 4.

FIGS. 5 to 12 are views sequentially illustrating operation principles of the sterilization system for a vehicle according to an embodiment of the present disclosure, and the configuration of embodiments of the present disclosure will be described with reference thereto.

The first shaft 120 of the outer housing 100 is set to be directed toward an irradiation target to which the sterilizing light L is irradiated, and when the driving unit 700 drives the outer housing 100, the outer housing 100 may be rotated about the first shaft 120. Accordingly, while the sterilizing light L is directed toward the interior trim T, an irradiation target to which the sterilizing light L is irradiated is changed by rotating the outer housing 100 and according to a rotation direction of the outer housing 100.

The inner housing 300 may have a spherical shape to be rotated relative to the outer housing 100 inside the outer housing 100, and the second shaft 320 of the inner housing 300 may be disposed to cross and intersect with the first shaft 120 of the outer housing 100. That is, the second shaft 320 and the first shaft 120 are set in a direction to intersect with each other with different axes. Accordingly, when the second shaft 320 is driven, the light transmitting portion 310 may be hidden, rather than being exposed to the inside of the vehicle, by rotating the inner housing 300.

The outer housing 100 may have a guide slit S1 extending along a rotational trajectory of the inner housing 300, the inner housing 300 may have a guide protrusion 330 protruding outwardly, and the guide protrusion 330 may slide while being guided by the guide slit S1 when the inner housing 300 is rotated. Accordingly, the inner housing 300 may be stably rotated, and also the outer housing 100 may remain stationary at the same position, without rotating, during the rotation of the inner housing 300.

Meanwhile, the system housing 900 may have an outer slit S2 formed to overlap the guide slit S1. The outer slit S2 may be formed with an extension S3 bent and extending in a lateral direction from an end of the outer slit S2. The guide protrusion 330 may slide while being guided by the outer slit S2 when the inner housing 300 is rotated, and may laterally slide while being guided by the extension S3 when the outer housing 100 is rotated. Accordingly, when the outer housing 100 is rotated after the inner housing 300 is rotated all the way to the end, the outer housing 100 may be stably rotated and the system housing 900 may remain stationary at the same position.

In summary, the light transmitting portion 310 may be exposed or not exposed to the interior space of the vehicle by rotating the inner housing 300 about the second shaft 320, and an irradiation target toward which the light transmitting portion 310 is directed in the interior space of the vehicle may be changed by rotating the outer housing 100 about the first shaft 120.

Specifically, the driving unit 700 may be connected to the first shaft 120 of the outer housing 100 through a first driving gear 742 and connected to the second shaft 320 of the inner housing 300 through a second driving gear 744. That is, the driving unit 700 may rotate in one direction to rotate the inner housing 300 first through the second driving gear 744, and continue to rotate in the one direction to rotate the outer housing 100 thereafter through the first driving gear 742.

Meanwhile, the driving unit 700 may include a motor 720 and a rotator 740 rotated by the motor, and the first driving gear 742 and the second driving gear 744 may be formed on an outer circumferential surface of the rotator 740 at positions spaced apart from each other in a circumferential direction. That is, the driving unit 700 includes only one motor 720 with which two-axis rotations can be implemented separately.

Specifically, a first pinion gear 140 may be provided on the first shaft 120 of the outer housing 100 and a second pinion gear 340 may be provided on the second shaft 320 of the inner housing 300. When the rotator 740 rotates, the first driving gear 742 may be connected to the first pinion gear 140 through a gear assembly G or the second driving gear 744 may be connected to the second pinion gear 340. Accordingly, even though the motor 720 rotates in one direction, the two different rotations may be separately performed by sequentially rotating the inner housing 300 and the outer housing 100 according to the rotation angle. This operation may also be identically implemented during reverse rotation when the sterilization system according to embodiments of the present disclosure is used or even not used.

Figure 6:
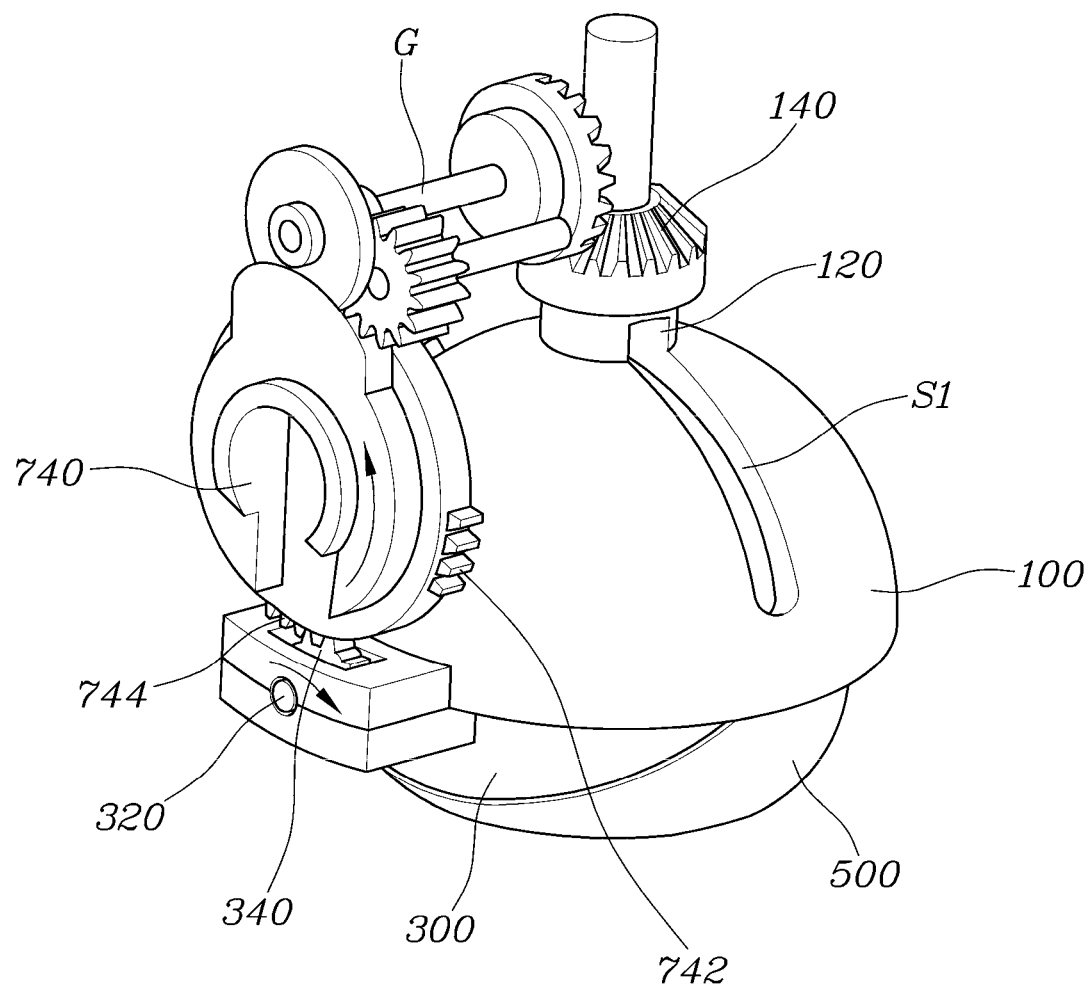
Figure 7:
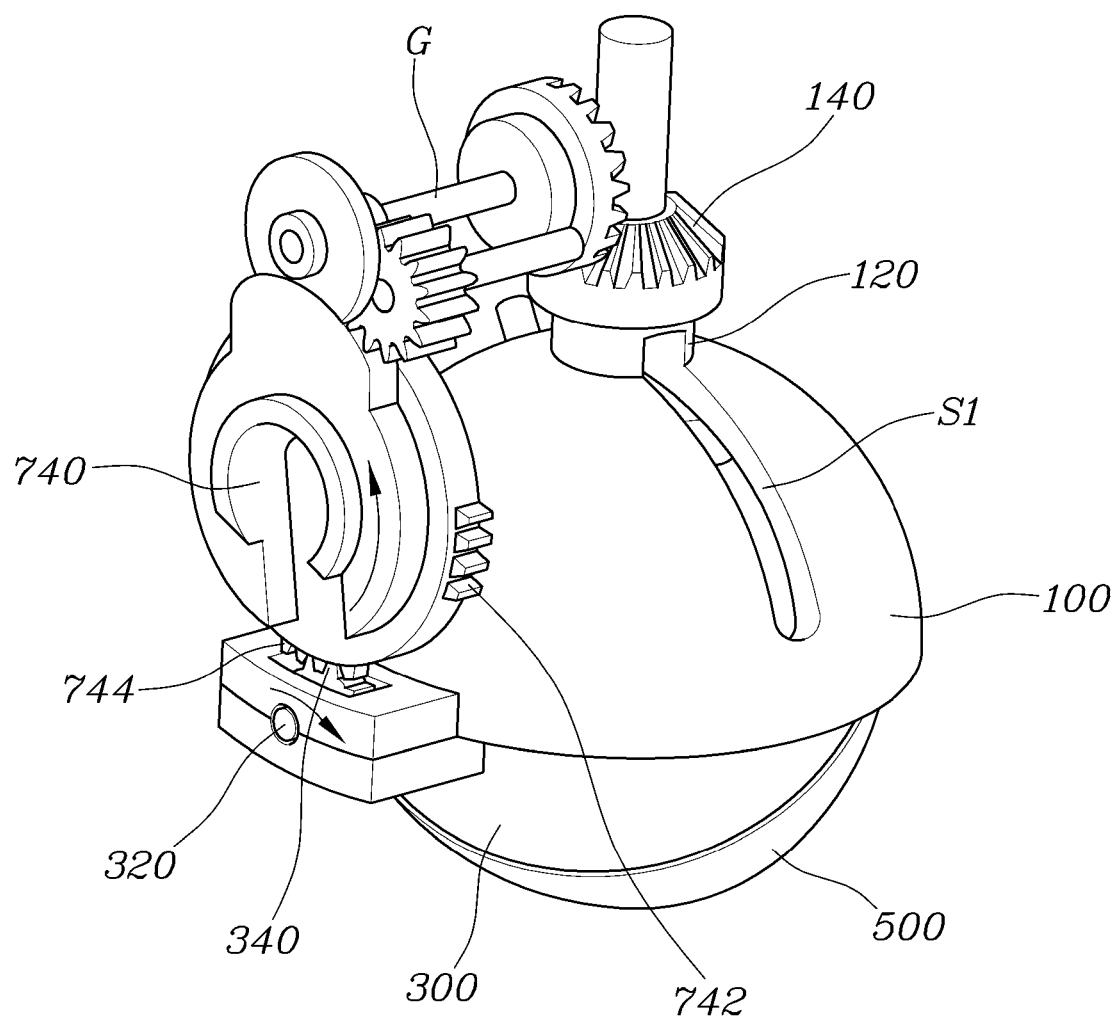
Figure 8:
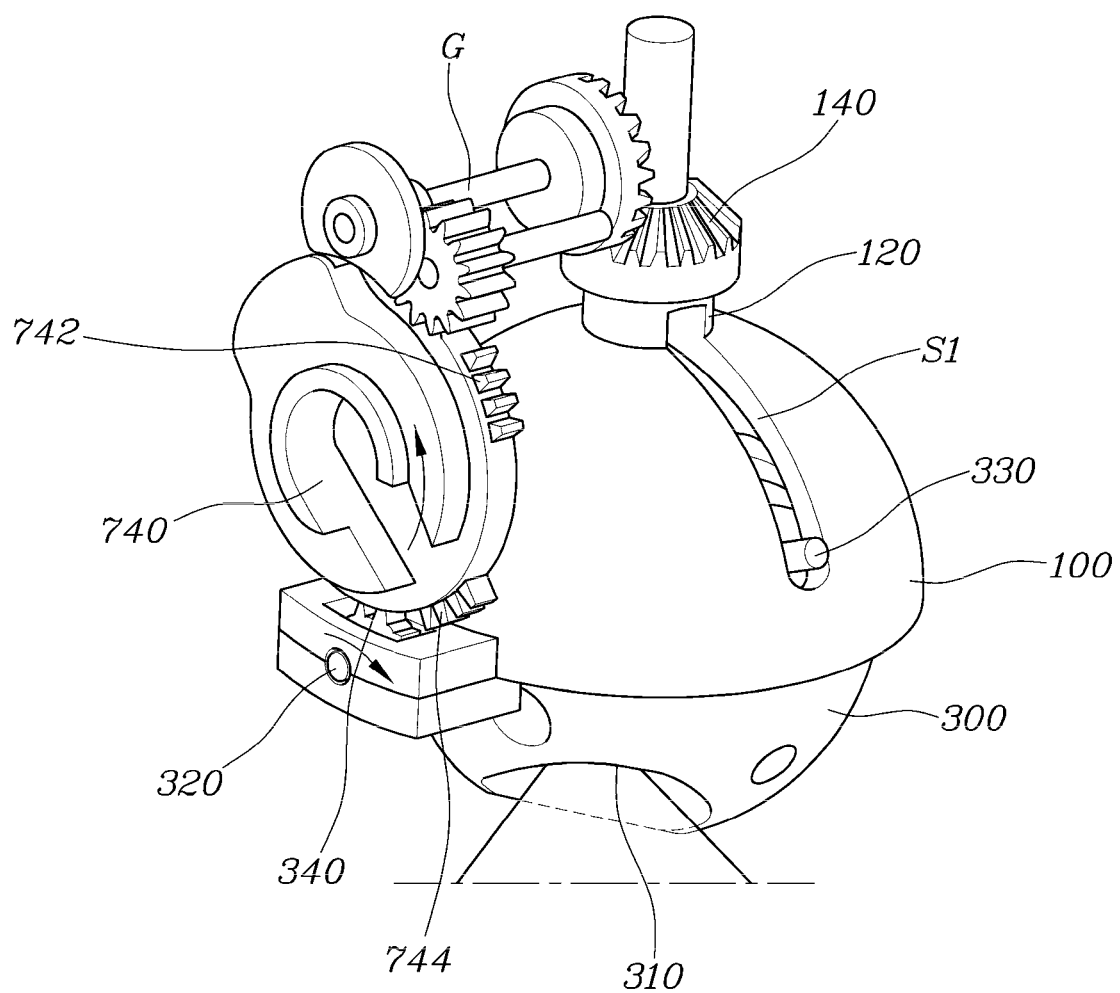
Figure 10:
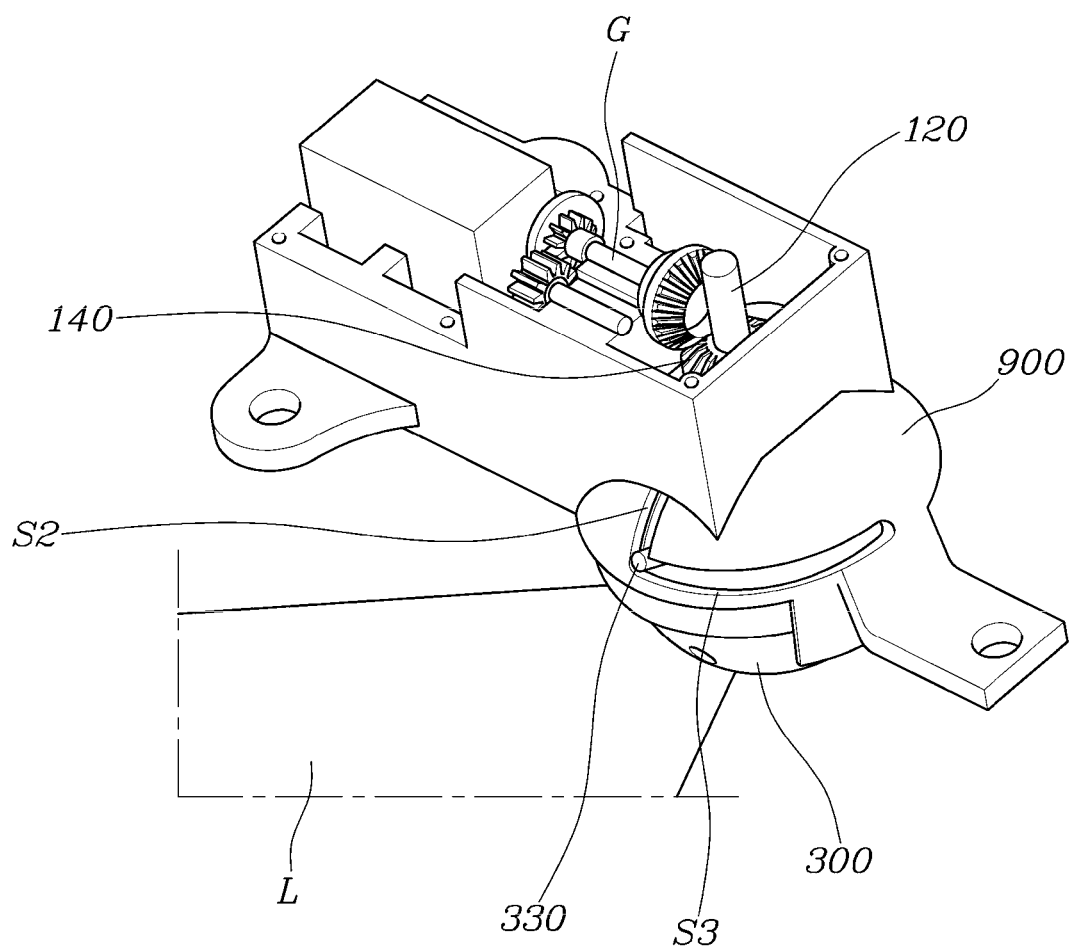

Specifically, when the rotator is rotated counterclockwise by driving the motor as illustrated in FIG. 6, the second driving gear 744 of the rotator is engaged with the second pinion gear 340 and the second pinion gear 340 is rotated clockwise. Accordingly, as illustrated in FIGS. 7 and 8, the inner housing 300 is rotated and the light transmitting portion 310 is exposed to the interior trim T. The sterilizing light L is irradiated by controlling the light source 520. The guide protrusion 330 slides while being guided by the guide slit S1, and at the same time, the guide protrusion 330 is also guided downwardly by the outer slit S2 of the system housing 900 as illustrated in FIG. 10.

Figure 9:
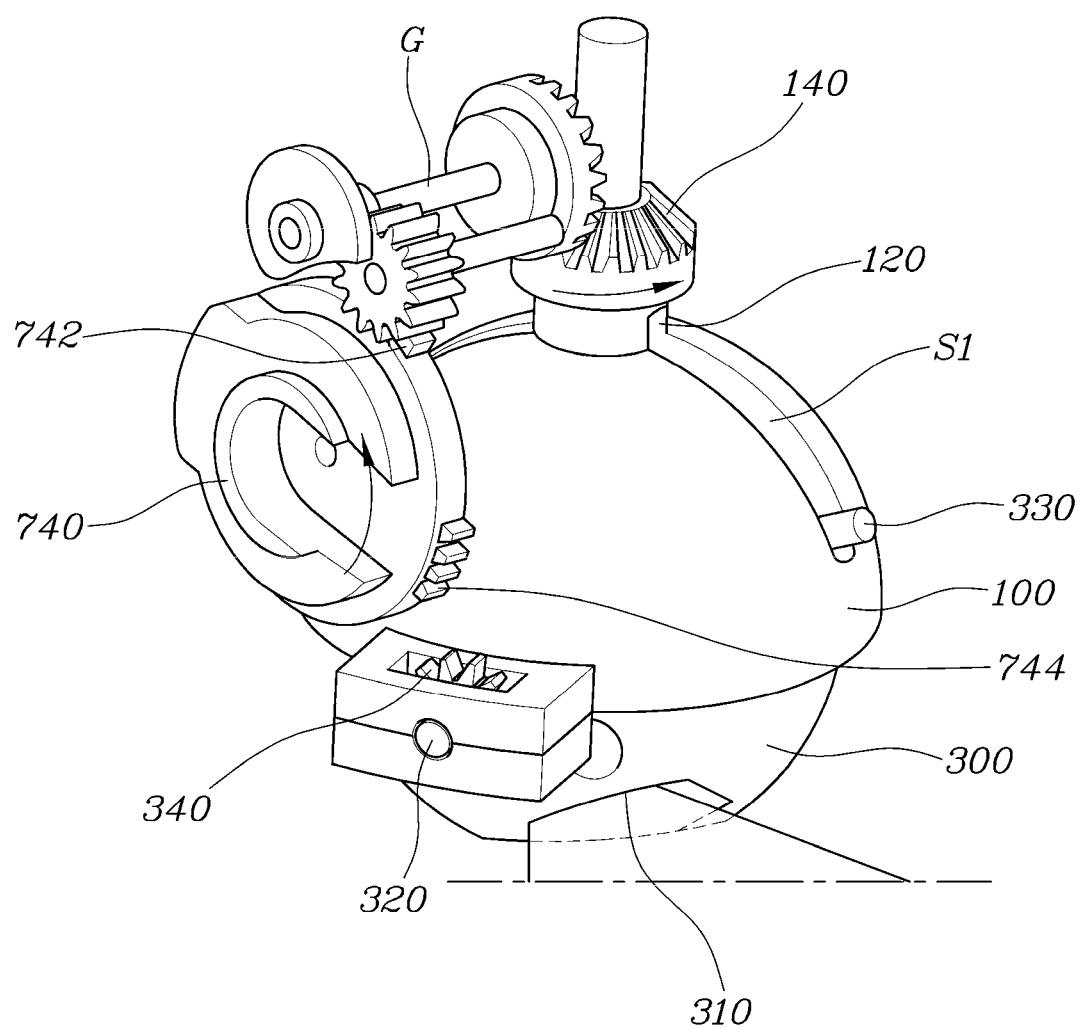
Figure 11:
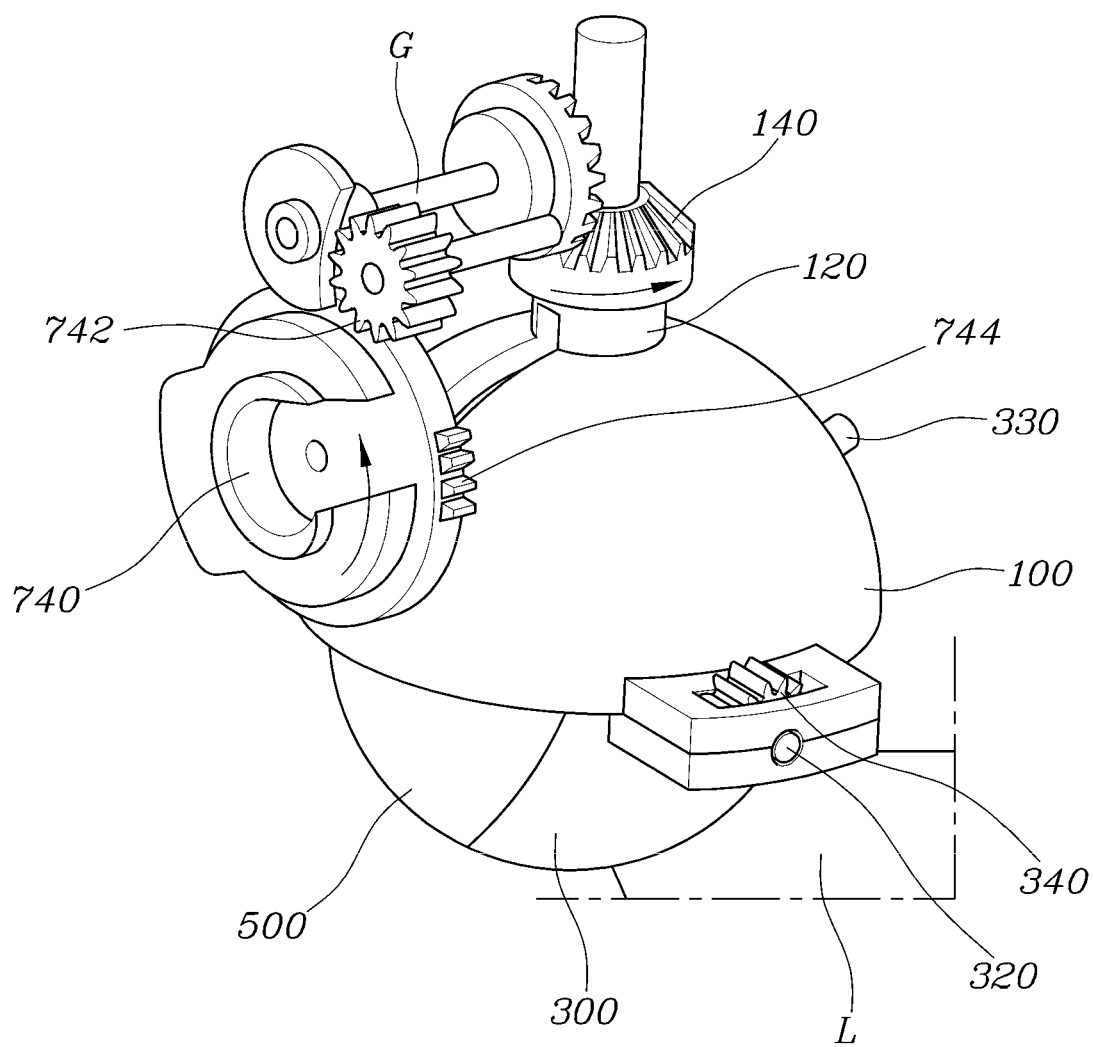
Figure 12:
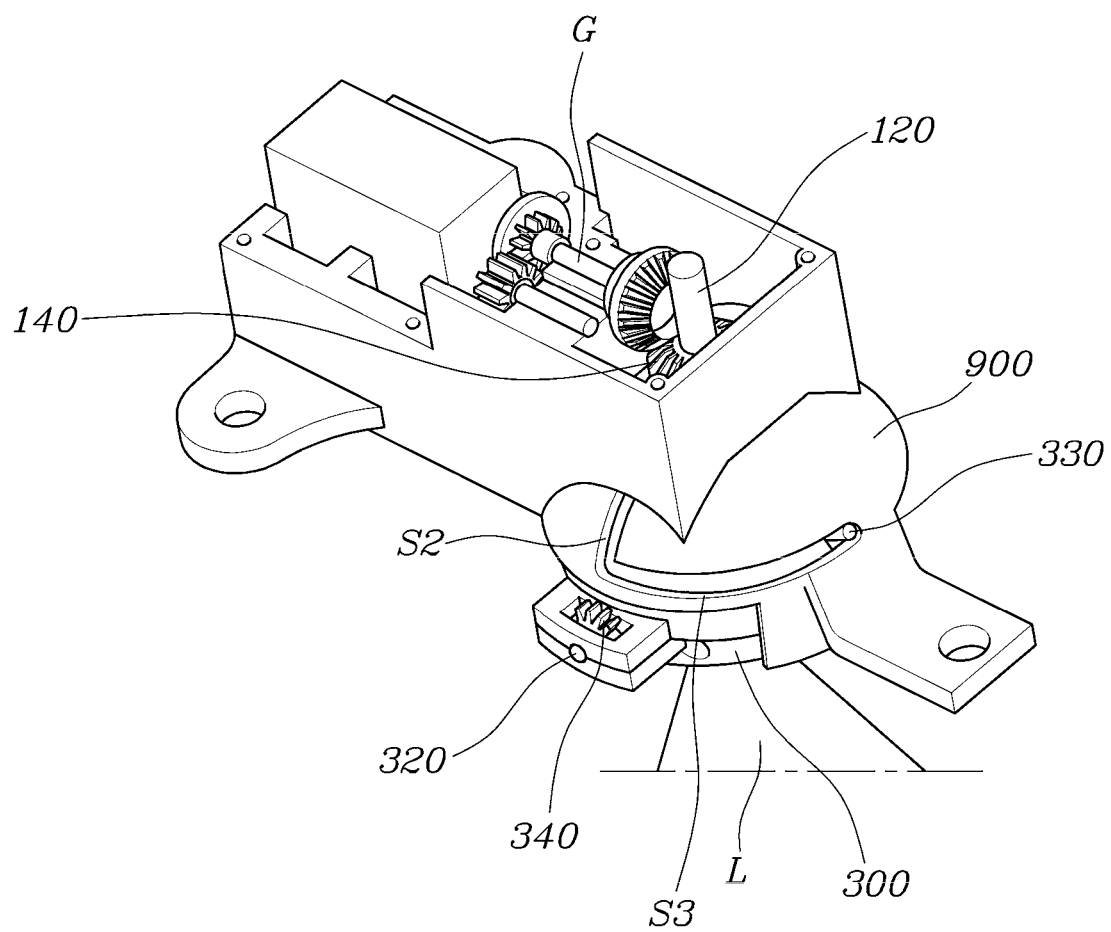

When the rotator 740 continues to rotate counterclockwise in that state, as illustrated in FIG. 9, the first driving gear 742 of the rotator is engaged with the gear assembly G, power is connected to the first pinion gear 140 of the outer housing 100 through the gear assembly G, and the first pinion gear 140 is rotated and the outer housing 100 is rotated accordingly, thereby shifting from the state of FIG. 9 to a state of FIG. 11. At this time, the guide protrusion 330 laterally slides along the extension S3 of the outer slit from the state of FIG. 10 to a state of FIG. 12.

When the sterilization system for a vehicle according to embodiments of the present disclosure described above is used together with a detection sensor detecting a human body, it may be detected whether or not a human body is approaching based on a change in capacitance or the like. If so, the light source may be controlled to be turned off, and the driving unit may be reversely rotated to return the sterilization system to the stored state. In addition, when the user is not in the vehicle, sterilization may be automatically performed, or sterilization may be performed by remotely controlling the sterilization system from a server through a user's mobile terminal.

The sterilization system for a vehicle according to embodiments of the present disclosure is capable of removing contamination caused by bacteria or the like in the inside of the vehicle, sterilizing several points at the same time, and preventing the user from feeling uncomfortable while being excellent in terms of design by forming a plane on the same level as the interior trim of the vehicle when the sterilization system is not used.

Although the present disclosure has been shown and described with respect to specific embodiments, it will be apparent to those having ordinary skill in the art that the present disclosure may be variously modified and altered without departing from the spirit and scope of the present disclosure as defined by the following claims.

What is claimed is:

1. A sterilization system for a vehicle, the sterilization system comprising:
    an outer housing configured to rotate about a first shaft and having an opening formed to face an interior space;
    an inner housing installed inside the outer housing exposed to the interior space through the opening, the inner housing configured to rotate about a second shaft, and having a light transmitting portion through which sterilizing light is to be transmitted, wherein the outer housing has a guide slit extending along a rotational trajectory of the inner housing and wherein the inner housing has a guide protrusion protruding outwardly, the guide protrusion being configured to slide while being guided by the guide slit when the inner housing is rotated;
    a light source embedded in the inner housing and configured to irradiate the sterilizing light toward the light transmitting portion; and a driver configured to rotate the outer housing and the inner housing to irradiate the sterilizing light to the interior space and to change an irradiation angle of the sterilizing light.

2. The sterilization system of claim 1, wherein the outer housing has a hemispherical shape with the opening and is inserted into an interior trim of the vehicle, the opening being disposed to face the interior space.

3. The sterilization system of claim 1, wherein the first shaft of the outer housing is set to be directed toward an irradiation target to which the sterilizing light is irradiated and the outer housing is configured to rotate about the first shaft.

4. The sterilization system of claim 1, wherein the inner housing has a spherical shape to be rotated inside the outer housing and the second shaft is disposed to cross and intersect with the first shaft.

5. The sterilization system of claim 1, further comprising a system housing surrounding the outer housing, wherein the system housing has an outer slit formed to overlap the guide slit, the outer slit is formed with an extension bent and extending in a lateral direction from an end of the outer slit, and the guide protrusion is configured to slide while being guided by the outer slit when the inner housing is rotated and laterally slide while being guided by the extension when the outer housing is rotated.

6. The sterilization system of claim 1, wherein the inner housing is configured to rotate about the second shaft to expose or not to expose the light transmitting portion to the interior space.

7. The sterilization system of claim 1, wherein the outer housing is configured to rotate about the first shaft to change an irradiation target toward which the light transmitting portion is directed in the interior space.

8. A sterilization system for a vehicle, the sterilization system comprising:
an outer housing configured to rotate about a first shaft and having an opening formed to face an interior space;
an inner housing installed inside the outer housing, exposed to the interior space through the opening, configured to rotate about a second shaft, and having a light transmitting portion through which sterilizing light is transmitted;
a light source embedded in the inner housing and configured to irradiate the sterilizing light toward the light transmitting portion; and
a driver configured to rotate the outer housing and the inner housing to irradiate the sterilizing light to the interior space and to change an irradiation angle of the sterilizing light, wherein the driver is connected to the first shaft of the outer housing through a first driving gear and connected to the second shaft of the inner housing through a second driving gear, wherein the driver includes a motor and a rotator configured to be rotated by the motor, and the first driving gear and the second driving gear are formed on an outer circumferential surface of the rotator at positions spaced apart from each other in a circumferential direction.

9. The sterilization system of claim 8, wherein the driver is configured to rotate in a first direction to rotate the inner housing first through the second driving gear, and continue to rotate in the first direction to rotate the outer housing thereafter through the first driving gear.

10. The sterilization system of claim 8, further comprising a first pinion gear provided on the first shaft of the outer housing and a second pinion gear provided on the second shaft of the inner housing, wherein when the rotator rotates, the first driving gear is configured to be connected to the first pinion gear or the second driving gear is configured to be connected to the second pinion gear.

11. The sterilization system of claim 8, wherein the outer housing has a hemispherical shape with the opening and is inserted into an interior trim of the vehicle, and the opening is disposed to face the interior space.

12. The sterilization system of claim 8, wherein the first shaft of the outer housing is set to be directed toward an irradiation target to which the sterilizing light is irradiated, and the outer housing is configured to rotate about the first shaft.

13. The sterilization system of claim 8, wherein the inner housing has a spherical shape to be rotated inside the outer housing, and the second shaft is disposed to cross and intersect with the first shaft.

14. A vehicle comprising:
a vehicle body that includes an interior space;
a system housing fixed to the vehicle body;
an outer housing provided in the system housing and configured to rotate about a first shaft and having an opening formed to face the interior space;
an inner housing installed inside the outer housing, exposed to the interior space through the opening, configured to rotate about a second shaft, and having a light transmitting portion through which sterilizing light is transmitted;
a light source embedded in the inner housing and configured to irradiate the sterilizing light toward the light transmitting portion; and
a driver configured to rotate the outer housing and the inner housing to irradiate the sterilizing light to the interior space and to change an irradiation angle of the sterilizing light, wherein the driver is connected to the first shaft of the outer housing through a first driving gear and connected to the second shaft of the inner housing through a second driving gear, and wherein the driver is configured to rotate in a first direction to rotate the inner housing first through the second driving gear, and continue to rotate in the first direction to rotate the outer housing thereafter through the first driving gear.

15. The vehicle of claim 14, wherein the outer housing has a hemispherical shape with the opening and is inserted into an interior trim of the vehicle, and the opening is disposed to face the interior space.

16. The vehicle of claim 14, wherein the first shaft of the outer housing is set to be directed toward an irradiation target to which the sterilizing light is irradiated, and the outer housing is configured to rotate about the first shaft.

17. The vehicle of claim 14, wherein the inner housing has a spherical shape to be rotated inside the outer housing, and the second shaft is disposed to cross and intersect with the first shaft.

18. The vehicle of claim 14, wherein:
the outer housing has a guide slit extending along a rotational trajectory of the inner housing, the inner housing has a guide protrusion protruding outwardly, and the guide protrusion is configured to slide while being guided by the guide slit when the inner housing is rotated; and
the system housing has an outer slit formed to overlap the guide slit, the outer slit is formed with an extension bent and extending in a lateral direction from an end of the outer slit, and the guide protrusion is configured to slide while being guided by the outer slit when the inner housing is rotated and laterally slide while being guided by the extension when the outer housing is rotated.

19. The vehicle of claim 14, wherein the inner housing is configured to rotate about the second shaft to expose or not to expose the light transmitting portion to the interior space.

20. The vehicle of claim 14, wherein the outer housing is configured to rotate about the first shaft to change an irradiation target toward which the light transmitting portion is directed in the interior space.

* * * * *